United States Patent
Ling et al.

(10) Patent No.: US 11,331,315 B2
(45) Date of Patent: May 17, 2022

(54) ARIPIPRAZOLE ORAL SOLUBLE FILM

(71) Applicant: Xiamen LP Pharmaceutical Co., Ltd., Xiamen (CN)

(72) Inventors: Rongbin Ling, Xiamen (CN); Lingyu Cai, Xiamen (CN); Fuxiang Lin, Xiamen (CN); Yong Yu, Xiamen (CN); Xiaojin Xiao, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 17/087,949

(22) Filed: Nov. 3, 2020

(65) Prior Publication Data
US 2022/0088009 A1    Mar. 24, 2022

(51) Int. Cl.
*A61K 31/496* (2006.01)
*A61K 9/00* (2006.01)
*A61K 9/70* (2006.01)

(52) U.S. Cl.
CPC .......... *A61K 31/496* (2013.01); *A61K 9/0056* (2013.01); *A61K 9/7007* (2013.01)

(58) Field of Classification Search
CPC ........................... A61K 9/7007; A61K 9/0056
See application file for complete search history.

(56) References Cited

U.S. PATENT DOCUMENTS

| 9,694,008 B2 | 7/2017 | Kim et al. |
| 2012/0149713 A1 | 6/2012 | Krekeler et al. |
| 2016/0022599 A1* | 1/2016 | Dave .................. A61K 9/0056 264/165 |

FOREIGN PATENT DOCUMENTS

| CN | 103690516 A | 4/2014 |
| CN | 103784426 B | 11/2015 |
| CN | 111939140 A * | 11/2020 |

* cited by examiner

*Primary Examiner* — Robert A Wax
*Assistant Examiner* — William Craigo
(74) *Attorney, Agent, or Firm* — Perkins Coie LLP; Viola T. Kung

(57) ABSTRACT

The present invention is directed to an aripiprazole oral soluble film and a preparation method thereof. The aripiprazole oral soluble film comprises 10-60% w/w of aripiprazole in a crystalline state and 30-95% w/w of one or more film-forming materials, wherein 90% of the aripiprazole particles have a size of ≤14.3 μm and are uniformly blended in the film without visible undispersed particles. The aripiprazole oral soluble film has excellent bioavailability, uniformity, stability, and palatability. The oral soluble film preparation is prepared by first grinding aripiprazole particles to have desired small particle sizes, then blending the aripiprazole particles with film forming materials in an aqueous solution to a uniform suspension, defoaming the suspension, and coating the suspension on a substrate and drying it to form a film.

8 Claims, No Drawings

ARIPIPRAZOLE ORAL SOLUBLE FILM

This application claims the priority of Chinese Application No. 202010995622.8, filed Sep. 22, 2020; which is incorporated herein by reference in its entirety.

FIELD OF INVENTION

The present invention relates to an oral soluble film for delivery of aripiprazole. The oral film contains aripiprazole particles in a low micron size and is a crystalline state. The oral film provides rapid dissolution of aripiprazole in mouth and is flexible and uniform in appearance.

BACKGROUND OF THE INVENTION

Schizophrenia is a common type of mental illness with delusions, hallucinations and complete separation from others. Schizophrenia is more prevalent than Alzheimer's disease, multiple sclerosis, insulin-dependent diabetes, and muscular dystrophy. According to World Health Organization data, schizophrenia continues to have the highest prevalence of any serious mental illness, affecting about 7‰ of adults worldwide.

The earliest antipsychotic drugs such as chlorpromazine, haloperidol, perphenazine, and sulpiride are known as typical or first-generation antipsychotic drugs (FGA). This type of drugs is gradually being replaced by second-generation antipsychotic drugs (SGA). SGA is also known as an atypical antipsychotic drug and is represented by clozapine, olanzapine, and risperidone, which are significantly better than the first-generation antipsychotic drugs in terms of safety and tolerability. However, long-term use of SGA can lead to weight gain and an increased tendency for abnormal lipid and glucose metabolism, thus leading to poor patient compliance with medication.

Aripiprazole, as the world's first partial dopamine agonist, can regulate dopamine levels without completely blocking the dopamine D2 receptor, and is also known as "third-generation antipsychotic drug" (TGA). It has clinical characteristics such as fast onset, high safety and good tolerance while having little effect on the levels of blood glucose, body weight and prolactin, so it can effectively improve the patient's compliance with long-term medication.

The currently marketed dosage forms are mainly ordinary tablets, orally disintegrating tablets, capsules, and long-acting injections. Due to the particularity of the patient population, the swallowing compatibility with ordinary tablets and capsules is poor, which limit patient compliance. As for the orally disintegrating tablets, the disadvantages include complicated preparation process, a large amount of excipients, high cost, low hardness, special packaging, inconvenient transportation and storage, and a grit feeling after oral administration. Long-acting injections have the problems of high production cost, inconvenient transportation and storage, and low patient compliance.

As a new oral drug delivery system, an oral soluble film is convenient to carry and use. It is suitable for patients who have difficulty in swallowing, which improves patient compliance. As a new dosage form, the form is attractive to patients who have difficulties with previously available options. Its unique method of administration can also greatly avoid concealment and vomiting by mental patients, and has advantages in the clinic.

The challenge in developing aripiprazole into an oral film is the low solubility of aripiprazole, content uniformity and discomfort (bitter taste) after film disintegration.

It has been reported that β-cyclodextrin is incorporated into injection solution to improve the solubility. However, the limited drug loading of the oral soluble film is insufficient to achieve the drug required amount.

U.S. Pat. No. 9,694,008 discloses an orally fast dissolving film formulation comprising aripiprazole or a pharmaceutically acceptable salt thereof and an organic acid, wherein: the film formulation has a pH in the range of 4.95 to 5.18; the aripiprazole or the pharmaceutically acceptable salt thereof and the organic acid have a weight ratio in the range of 2:1 to 66:1; the organic acid is citric acid. The '008 patent uses organic acids to control the pH within a narrow range of 4.95 to 5.18 to improve solubility. Such narrow pH range is difficult to control for manufacturing. Different saliva levels of different individuals also influence on the and affect the drug release rate in individuals.

There exists a need for a new and improved oral soluble film of aripiprazole, which achieves ideal dissolution, uniformity, stability, scalability, and patient compliance.

DETAILED DESCRIPTION OF THE INVENTION

The present invention provides aripiprazole oral soluble film with improved drug dissolution, uniformity, and taste. The inventors have discovered that by controlling the aripiprazole particle size and the crystalline state in the oral film, the film provides a desirable aripiprazole dissolution rate in the oral cavity and a comparable bioavailability to that of an aripiprazole tablet. The film has a good stability and a desirable taste. The aripiprazole oral soluble film is placed in the oral cavity of a subject, dissolved in saliva, and then swallowed and absorbed in the gastrointestinal tract.

The oral soluble film of the present invention uses small particle size of aripiprazole ($D_{90}$: 14.3 μm) to maximize the specific surface area to achieve rapid dissolution, without adding plasticizers, stabilizers, surfactants, or clathrates into the formulation. The production process does not require an organic solvent which improves to environmental protection and safety. Since the particle size is extremely small, the film does not produce a sense of grain and provides a good palatability.

The aripiprazole oral soluble film of the present invention comprises 0.5-70% w/w of aripiprazole in a crystalline state and 25-96% w/w of one or more film-forming materials, wherein 90% of the aripiprazole particles have a size of <14.3 μm and are uniformly blended in the film without visible undispersed particles.

The aripiprazole oral soluble film comprises aripiprazole, or a pharmaceutically acceptable salt thereof, in a small particle size of $D_{90}$ being 14.3 μm. "$D_{90}$" as used herein, means 90% of the particles have a diameter below the recited value. For example, $D_{90}$ of 14.3 μm means that 90% of the particles have a diameter below 14.3 μm.

The commercially available aripiprazole typically has a particle size of 65-100 μm. When aripiprazole with a particle size of $D_{90}$: 30 to 100 μm was used to prepare an oral soluble film, the film was non-uniform in appearance due to drug sedimentation during film formation; the film had an unacceptably slow dissolution rate and a grit-like taste when it was dissolved in mouth.

Aripiprazole in the oral soluble film in general is in an amount of about 10-70% w/w, preferably about 10-65%, or about 15-65%, or about 20-65% w/w. The $D_{90}$ particle size of aripiprazole in general is about 14 μm, preferably about 12 μm or about 10 μm. "About" as used herein, refers to ±10% of the recited value. About 90% of aripiprazole particles in the oral soluble film have a size distribution of about 0.1-14 µm, about 0.1-12 µm, or about 0.1-10 µm.

Aripiprazole in the oral soluble film of the present invention is in a crystalline state. The inventors have discovered that when the drug substance aripiprazole is in an amorphous form, aripiprazole dissolves in the oral cavity too quickly and results in a bitter taste. Moreover, the stability of aripiprazole is reduced noticeably due to the amorphous form. The present invention combines the features of small particles and crystalline state of aripiprazole and provides an oral film with a good dissolution rate, a palatability, and a uniform and flexible film.

The film-forming materials useful in the pharmaceutical composition include, but not limited to, polyvinyl alcohol (PVA), hydroxypropyl cellulose (HPC), hydroxyethyl cellulose, hydroxypropyl methyl cellulose, hypromellose (HPMC), sodium carboxymethyl cellulose (CMC-Na), xanthan gum, pectin, copovidone, povidone, guar gum, pullulan, polyethylene oxide, sodium alginate, and chitosan. Preferred film-forming materials are polyvinyl alcohol, hypromellose, hydroxypropyl cellulose, hydroxyethyl cellulose, copovidone, povidone, pullulan, polyethylene oxide. More preferred film-forming materials are polyvinyl alcohol, hypromellose, hydroxypropyl cellulose, and hydroxyethyl cellulose. The weight percentage of film-forming materials is about 25-96%, 30-96%, 35-96%, 25-80%, 30-80%, or 35-80% w/w. The film-forming materials are compatible with aripiprazole and provide a suitable drug loading capacity.

In one embodiment, the film of the present invention further comprises a defoamer to improve the defoaming efficiency of film-forming solution and flexibility of the film. In general, the defoamer is in an amount of about 0.01-10% or 0.02-5% w/w, preferably about 0.05-5%, about 0.05-2%, about 0.05-1%, or about 0.1-0.5% w/w. In one embodiment, the defoamer is selected from the group consisting of dimethicone, simethicone, oleyl alcohol, and a combination thereof.

One or more coloring agents are optionally added to the film-forming materials to improve the color of the oral soluble film. The coloring agent, for example, are selected from the group consisting of FD&C colors, D&C colors, and combinations thereof.

One or more flavoring agents or taste masking agents are optionally added to improve the taste of the oral soluble film. The flavoring agent may include one or more ingredients as follows: sucrose, glucose, sodium saccharin, fructose, xylitol, stevia, aspartame, sucralose, neotame and acesulfame potassium, peppermint oil, menthol, orange flavor, pineapple flavor, cherry flavor, apple flavor, banana flavor, blueberry flavor, peach flavor, mango flavor, or grape flavor. Sucralose and menthol are preferred flavoring agents for the present invention. The amount of a flavoring agent in the composition is about 0.01-5%, preferably about 0.05-2% (w/w) in the film forming solution and in the film.

The oral film of the present invention does not include a plasticizer or a surfactant. Plasticizer are typically used to improve the flexibility of a film, and surfactants are typically used to increase the solubility of aripiprazole. Because the present invention uses small particles ($D_{90}$: 14 µm) of aripiprazole, the film forming solution has a good solubility of aripiprazole, and the film has a good flexibility without a plasticizer or a surfactant.

The oral film of the present invention does not include an organic solvent. Organic solvents are sometimes used to improve the solubility of aripiprazole. Because the present invention uses small particles ($D_{90}$: 14 µm) of aripiprazole, the film forming solution has a good solubility of aripiprazole without an organic solvent. In one embodiment, the oral film further does not include an organic acid such as citric acid.

The present invention is also directed to a process for preparing the aripiprazole oral soluble film. The process comprises the steps of: (a) grinding a starting material of aripiprazole by bead milling, air crushing, or colloid milling until 90% of the aripiprazole particles have a size of ≤14.3 µm, (b) blending the aripiprazole particles of (a) and one or more film-forming materials in an aqueous solution by a mechanical homogenization blending process at a speed of at least 1500 rpm, optionally further by plate- and frame blending, to prepare a uniform suspension, (c) defoaming the suspension; and (d) coating the defoamed suspension on a substrate and drying the suspension to form the film.

In step (a), a starting material of aripiprazole (typically having $D_{90}$ of 50-100 µm) was grinded until the aripiprazole particles reach desirable smaller sizes of $D_{90}$: 14.3 µm and maintain a crystalline state. Normal tooth mill, knife mill and high-pressure homogenization processes cannot obtain the required particle size, while bead milling, air-guided crushing and colloidal milling processes can reduce the particle size $D_{90}$ to 14.3 µm and maintain the original crystal form. A preferred mill process is bead milling with a scatter axis speed of ≥3000 rpm (e.g., 3000-6000 rpm) and milling cycles ≥3 cycles.

The issues of aripiprazole including slow dissolution rate, grit-like taste and stability problems can be resolved by a special milling process, but due to the strong electrostatic adsorption of small aripiprazole particles, they tend to adsorb together and aggregate into agglomerates. Furthermore, aripiprazole is a poorly soluble non-ionic compound, especially in the case of fine particle size with a large surface tension, it is difficult to have a even suspension. Step (b) resolves these problems.

In step (b), the aripiprazole particles of smaller sizes, one or more film-forming materials, and optionally a defoamer are blended in an aqueous solution by homogenization blending to prepare a uniform film-forming suspension. Different blending processes can lead to different blending uniformity. The conventional paddle blending, plate and frame blending, and paddle blending plus plate-and-frame blending do not achieve the required blending uniformity. However, homogenization blending or homogenization blending plus plate-and-frame blending fully disperses the aripiprazole crystal particle agglomerates to form a uniform suspension, without a need to add surfactants or emulsifiers. To form a homogeneous suspension, a preferred homogenization speed is at least 1500 rpm (e.g., 1500-4000 rpm or 1500-3000 rpm) and preferred homogenization time is at least 3 minutes (e.g., 3-20 minutes). Conduct a defoaming process to obtain the homogeneous film forming solution.

In step (c), the blended suspension of (b) is defoamed. In the formulation, aripiprazole is in the crystalline form with a high specific gravity, which leads to sedimentation during the defoaming process. Although, adding a suspending agent or thickening agent can slow down the settling rate, it also prolongs the defoaming time. Therefore, defoaming agents, which increase the surface tension and accelerate the bursting of bubbles, are preferably used together with vacuum defoaming technique to reduce the defoaming time. With preferred defoaming agents (e.g., dimethicone, simethicone, or oleyl alcohol) and vacuum defoaming process, the defoaming time is shortened by more than 8 h, while the film-forming ability and stability of the film is maintained. A defoaming agent may further hinder the sedimentation of aripiprazole, while improving the production efficiency and reducing production costs.

In step (d), the defoamed suspension is coated on a substrate such as a conveyer and is dried to form a film. The dried film is ready to be cut and packaged.

The advantages of the oral soluble film of the present invention are summarized below:

a. As the aripiprazole remains original crystal form and degree of crystallinity, the stability of the drug substance is maintained and no extra stabilizer is required in the formulation.

b. The dissolution rate of aripiprazole is increased dramatically: ≥85% or even ≥95% is dissolved within 5 minutes.

c. Due to the small particle size of the drug substance, the sedimentation of aripiprazole during the solution preparing, defoaming, coating and drying processes is effectively reduced. Thus, desired uniformity can be achieved in the final film product.

d. Combining with a homogenization process, the drug load percentage is improved to 60% w/w without using any plasticizer.

e. As the particle size of the drug substance is extremely small, no grit-like taste or any other uncomfortable feeling develops after the film is dissolved in the oral cavity, which improves taste.

f. The oral soluble film formed is flexible and not brittle without the use of plasticizers.

The following examples further illustrate the present invention. These examples are intended merely to be illustrative of the present invention and are not to be construed as being limiting.

EXAMPLES

Example 1: Aripiprazole Soluble Film (30-100 μm Particle Size with Crystalline State)

In this example, the aripiprazole (Particle Size $D_{90}$: 65.5 μm) was manufactured as a film dosage form, which can be administered orally. The formulation of this example is shown below.

| Aripiprazole | 5.0 mg (25% w/w) |
| Hypromellose | 14.6 mg (73% w/w) |
| Titanium Dioxide | 0.4 mg (2% w/w) |
| Purified Water | 45 mg (Removed during manufacturing process) |

Preparation: Aripiprazole was dispersed into the solvent according to the formulation, then it was added with other components in the formulation, and blended until it was completely suspended by paddle blending process. The film solution was defoamed and evenly coated on the conveyor belt, and then dried at the temperature of about 50° C. to 80° C. Residual aqueous carrier was evaporated after drying. After the film was formed, it was cut into a suitable size and shape and packaged.

The aripiprazole soluble film prepared by the above method presented satisfactory film-forming performance and could be easily peeled off from the film base. Also, the films had smooth appearance and uniform color. Moreover, the active ingredient aripiprazole crystal powder was dispersed evenly in the film. An x-ray powder diffraction showed that the aripiprazole was in a crystallized state in the film.

In a dissolution test, the drug powder was released and dissolved after the oral film was dissolved, and the dissolution rate was relatively slow (41% at 5 min).

TABLE 1

Dissolution Test Result (Crystalline Aripiprazole)

Media
pH 4.0 sodium acetate buffer (1000 mL),
basket method, speed: 75 rpm

| | Time (min) | | | | |
|---|---|---|---|---|---|
| | 3 | 5 | 10 | 15 | 30 |
| Dissolved (%) | 27 | 41 | 68 | 76 | 98 |

Soluble films having different particle sizes (D90: 30-100 μm) of aripiprazole were prepared by the same method and tested by the dissolution test. The results show that aripiprazole in the produced soluble film was all in a crystalline state and was dispersed in the film as spots. Those soluble films also had a slow dissolution profile of 23%-72% at 5 min.

Example 2: Aripiprazole Soluble Film (Amorphous State)

In this example, the aripiprazole soluble film was prepared based on the method stated in Example 1. The formulation was modified to use methylene chloride instead of purified water. Aripiprazole used in the formulation was in a crystalline state, however, after the film was prepared, aripiprazole was converted into an amorphous state within the film, due to the use of methylene chloride in the formulation.

| Aripiprazole | 5.0 mg (25% w/w) |
| Hypromellose | 14.6 mg (73% w/w) |

-continued

| | |
|---|---|
| Titanium Dioxide | 0.4 mg (2% w/w) |
| Methylene Chloride | 45 mg (Removed during manufacturing process) |

The aripiprazole soluble film prepared by this example had a smooth appearance and uniform color, without any noticeable crystal solid in the film. An x-ray powder diffraction test was conducted on this sample and suggested that the aripiprazole was in an amorphous state. Furthermore, the dissolution test showed that the drug substance was rapidly dissolved with 97% dissolved in 3 min.

TABLE 2

Dissolution Test Result (Amorphous Aripiprazole)

Media
pH 4.0 sodium acetate buffer (1000 mL),
basket method, speed: 75 rpm

| | Time (min) | | |
|---|---|---|---|
| | 3 | 5 | 10 |
| Dissolved (%) | 97 | 99 | 100 |

In an accelerated stability experiment performed on the film, an undesired related substance (RS) F increased above the acceptance criteria (≤0.3%) after 3 months as shown in Table 3. Furthermore, because it was in an amorphous state, aripiprazole was fully and rapidly dissolved during dissolution of the film in the mouth, and the palatability was not good with a bitter taste. In addition, an organic solvent of methylene chloride was used during the process, which is not desirable.

TABLE 3

Accelerated Stability Result

| Accelerated Condition (40° C., 75% RH) | Acceptance Criteria | Example 2 |
|---|---|---|
| 0 day | RS F ≤ 0.3% | RS F: 0.03% |
| | RS G ≤ 0.3% | RS G: 0.02% |
| | Total ≤ 1.0% | Total: 0.08% |
| 1 Month | | RS F: 0.17% |
| | | RS G: 0.09% |
| | | Total: 0.29% |
| 3 Month | | RS F: 0.37% |
| | | RS G: 0.19% |
| | | Total: 0.57% |

*Note:
RS F: USP Aripiprazole Related Compound F RS, $C_{23}H_{27}Cl_2N_3O_3$
RS G: USP Aripiprazole Related Compound G RS, $C_{23}H_{25}Cl_2N_3O_2$ Example 3: Aripiprazole Milling Processes This experiment was to test particle size distribution of aripiprazole prepared by different milling processes.

In this experiment, aripiprazole with particle size distribution of $D_{90}$: 173.3 μm was used as a starting material. The starting material aripiprazole was grinded by different processes of tooth milling process, knife milling process, high-pressure homogenization process, air crushing process, colloid milling process, and bead milling process. The description and parameters of each process and the resulting particle size $D_{90}$ are shown in Table 4. The results show that among the milling processes tested, the bead milling process provided the smallest particle size of $D_{90}$: 1.3 μm. Air crushing and colloid milling also provided small particle size of $D_{90}$<10 μm.

TABLE 4

The Particle Size Distribution of Aripiprazole Obtained by Different Milling Processes

| Milling Processes | Tooth Milling | Knife Milling | High-Pressure Homogenization | Air Crushing | Colloid Milling | Bead Milling |
|---|---|---|---|---|---|---|
| Process Description | Through high-speed relative movement between the movable toothed plate and the fixed toothed plate, the materials are crushed by impact and friction | Through the high-speed rotation of the shearing knife, the materials are crushed by impact, friction and impact of materials. | Forcing the materials at high pressure through small holes, and crush the materials into small particle sizes | Use high-speed airflow to make particles impact, collide, friction and shear to achieve crushing | Colloid mills work on the rotor-stator principle: a rotor turns at high speeds | Beads inside the grinding chamber are agitated by rotating the shaft, and the particles are ground by the collision and shear force of the beads. |
| Process Parameters | Milling at 3500 rpm and sieved with 250 mush screen | Milling for 10 min at 25000 rpm | Homogenization for 5 cycles at 20000 Psi pressure and 2 L/h flow rate | Milling at 5.0 kg/cm² air pressure and 1 kg/h feed rate | Milling for 5 cycles at 10000 rpm | Milling for 5 cycles at 6000 rpm |
| $D_{90}$ | 56.4 μm | 16.6 μm | 38.9 μm | 9.3 μm | 7.2 μm | 1.3 μm |

Example 4: Aripiprazole Bead Milling Process with Different Process Parameters

This experiment is to test particle size distribution of aripiprazole prepared by beading milling with different process parameters.

In this experiment, aripiprazole with particle size distribution ($D_{90}$: 56.2 μm) was used as a starting material. The bead milling process was used for milling, with different process parameters (different spindle speed and numbers of grinding cycles) as shown in Table 5. When the spindle speed was ≥3000 rpm, and the number of grinding cycles was ≥3 cycles, a satisfactory particle size distribution ($D_{90}$≤8.3 μm) was obtained. With a lower spindle speed of 1500 rpm, but a higher number of grinding cycles of ≥5 cycles, a satisfactory particle size distribution ($D_{90}$≤14.3 μm) can also be obtained.

TABLE 5

The Particle Size Distribution of Aripiprazole Obtained by Different Process Parameters

| Process | Spindle Speed | | | | | | | |
|---|---|---|---|---|---|---|---|---|
| | 1000 rpm | 1500 rpm | 1500 rpm | 1500 rpm | 3000 rpm | 3000 rpm | 6000 rpm | 6000 rpm |
| | Grinding cycles | | | | | | | |
| Parameters | 20 | 3 | 5 | 10 | 3 | 5 | 3 | 10 |
| $D_{90}$ | 18.6 μm | 23.5 μm | 14.3 μm | 10.2 μm | 8.3 μm | 4.7 μm | 1.8 μm | 0.5 μm |

Example 5: Aripiprazole Soluble Film (0.5-18.6 μm Particle Size)

In this example, aripiprazole of different particle size $D_{90}$: 0.5 μm, 1.3 μm, 4.7 μm, 10.2 μm, 12.4 μm, 14.3 μm and 18.6 μm) was prepared by bead milling process. The soluble film was prepared via the method of Example 1, with the formulation below.

| | 5-1 | 5-2 | 5-3 | 5-4 | 5-5 | 5-6 | 5-7 |
|---|---|---|---|---|---|---|---|
| | Particle Sizes ($D_{90}$) | | | | | | |
| | 0.5 μm | 1.3 μm | 4.7 μm | 10.2 μm | 12.4 μm | 14.3 μm | 18.6 μm |
| Aripiprazole | 5.0 mg (25% w/w) | | | | | | |
| Hypromellose | 14.6 mg (73% w/w) | | | | | | |
| Titanium Dioxide | 0.4 mg (2% w/w) | | | | | | |
| Purified Water | 45 mg (Removed during manufacturing process) | | | | | | |

The aripiprazole soluble film prepared by the above method presented satisfactory film-forming performance and could be easily peeled off from the film base. Also, the films had a smooth appearance and uniform color, but there were some visible agglomerate particles on the film which were not completely evenly dispersed. An x-ray powder diffraction showed that the aripiprazole was in a crystallized state within the film.

The aripiprazole soluble films were tested by dissolution tests. The results show that when the particle sizes of $D_{90}$ were ≤14.3 μm, the dissolution was rapid, with ≥86% dissolved at 5 min (86%-100%).

TABLE 6

Dissolution Test Result

| | | pH 4.0 sodium acetate buffer (1000 mL), basket method, speed: 75 rpm | | |
|---|---|---|---|---|
| | Particle Sizes | Dissolved (%) | | |
| Test | ($D_{90}$) | 3 min | 5 min | 10 min |
| Example 5-1 | 0.5 μm | 96 | 100 | 100 |
| Example 5-2 | 1.3 μm | 95 | 100 | 99 |
| Example 5-3 | 4.7 μm | 90 | 97 | 100 |
| Example 5-4 | 10.2 μm | 85 | 93 | 99 |

TABLE 6-continued

Dissolution Test Result

| | | pH 4.0 sodium acetate buffer (1000 mL), basket method, speed: 75 rpm Dissolved (%) | | |
|---|---|---|---|---|
| | Particle Sizes | | | |
| Test | ($D_{90}$) | 3 min | 5 min | 10 min |
| Example 5-5 | 12.4 μm | 82 | 91 | 97 |
| Example 5-6 | 14.3 μm | 77 | 86 | 95 |
| Example 5-7 | 18.6 μm | 64 | 81 | 91 |

An accelerated stability experiment was performed on film prepared according to Example 5-2; all related substances were well within the acceptance criteria during the accelerated period as shown in Table 7.

TABLE 7

Accelerated Stability Result

| Accelerated Condition (40° C., 75% RH) | Acceptance Criteria | Example 5-2 |
|---|---|---|
| 0 day | RS F ≤ 0.3% RS G ≤ 0.3% Total ≤ 1.0% | RS F: 0.02% RS G: 0.01% Total: 0.04% |
| 1 Month | | RS F: 0.03% RS G: 0.02% Total: 0.05% |
| 3 Month | | RS F: 0.03% RS G: 0.02% Total: 0.07% |

*Note:
RS F: USP Aripiprazole Related Compound F RS, $C_{23}H_{27}Cl_2N_3O_3$
RS G: USP Aripiprazole Related Compound G RS, $C_{23}H_{25}Cl_2N_3O$ Example 6: Blending Processes Because aripiprazole has a strong electrostatic adsorption, it easily aggregates into agglomerates. Further, aripiprazole is a poorly soluble nonionic compound and has a large surface tension in a submicron particle size, so it is not easy to suspend aripiprazole into an aqueous solution effectively and evenly. This example tested different blending methods and evaluate the blend uniformity.

In this example, aripiprazole (particle Size $D_{90}$: 1.3 μm) soluble film was prepared via the method according to Example 5-2, except with different blending processes, with the formulation below.

| Aripiprazole | 5.0 mg (25% w/w) |
|---|---|
| Hypromellose | 14.6 mg (73% w/w) |
| Titanium Dioxide | 0.4 mg (2% w/w) |
| Purified Water | 45 mg (Removed during manufacturing process) |

Each aqueous aripiprazole formulation was blended by a different blending process of paddle blending, plate and frame blending, paddle blending plus plate-and-frame blending, and homogeneous blending plus plate-and-frame blending process. Homogeneous blending is conducted by a rotor/stator mixer. Through the high-speed and stable rotation of the rotor, high liquid shear, friction, extrusion, and collision are formed in the gap between the stator and the rotor, make the solid powder uniformly dispersed in the liquid. Homogenization blending is a preferred blending method for the present invention.

The uniformity test results are shown in Table 8. Blend uniformity is the uniformity of the suspension after blending. In this example, immediately after the blending process, 10 samples were taken from different locations of the blending tank and the aripiprazole amount of each sample was measured and the relative standard deviation (RSD) of blend uniformity was calculated.

RSD is calculated by the formula below:

$$RSD = \frac{S}{\bar{x}} \times 100\% = \frac{\sqrt{\frac{\sum_{i=1}^{n}(x_i - x)^2}{n-1}}}{x} \times 100\%$$

Where S is standard deviation, $\bar{X}$ is arithmetic mean of all results, Xi is measured result of each sample, n is total number of samples.

The results of Table 8 show that a homogenization blending plus plate-and-frame blending process achieved a satisfactory blend uniformity in the aqueous suspension and provided a uniform film appearance.

TABLE 8

Uniformity Test Result

| Blending Method | Paddle Blending | Plate and Frame Blending | Paddle Blending plus Plate-and-Frame Blending | Homogenization Blending plus Plate-and-Frame Blending |
|---|---|---|---|---|
| Process Description | The motor drives the paddle to form an axial liquid flow, circulate the liquid and mix the material | The shape of the plate and frame is consistent with the inner wall of the tank, and the gap from the inner wall | Combining paddle blending and plate-and-frame blending methods | Combining homogeneous blending and plate-and-frame blending methods |

TABLE 8-continued

Uniformity Test Result

| Blending Method | Paddle Blending | Plate and Frame Blending | Paddle Blending plus Plate-and-Frame Blending | Homogenization Blending plus Plate-and-Frame Blending |
|---|---|---|---|---|
| | | is small, which is suitable for the stirring of medium and high viscosity liquids | | |
| Process Parameters | Blending for 30 min at 1500 rpm | Blending for 30 min at 30 rpm | Blending for 30 min at paddle stirring speed of 1500 rpm and plate-and-frame stirring speed of 30 rpm | Blending for 30 min at homogenization speed of 1500 rpm and plate-and-frame stirring speed of 30 rpm |
| Suspension State | There are lot of agglomerates that are not completely dispersed, and some powder is floating on the surface of the mixing tank. | There are few agglomerates that are not completely dispersed, and some powder is floating on the surface of the mixing tank. | There are few agglomerates that are not completely dispersed | Uniform suspension, no visible aggregate particles, no residual powder on the liquid surface |
| Blend Uniformity in Suspension RSD* (n = 10) | 7.1% | 5.8% | 4.7% | 0.8% |
| Appearance of Dry Film | Has a lot of visible agglomerated particles on the film | Has a few visible agglomerated particles on the film | Has a few visible agglomerated particles on the film | Uniform film without visible undispersed particles |

*Relative Standard Deviation [<3% is acceptable]

Example 7: Homogenization Process

In this example, the aripiprazole (Particle Size $D_{90}$: 1.3 μm) soluble film was prepared via the method of Example 5-2 with the formulation below, except with homogeneous blending plus plate- and frame blending.

| | |
|---|---|
| Aripiprazole | 5.0 mg (25% w/w) |
| Hypromellose | 14.6 mg (73% w/w) |
| Titanium Dioxide | 0.4 mg (2% w/w) |
| Purified Water | 45 mg (Removed during manufacturing process) |

The blend uniformity test results from samples obtained under different process parameters is shown in Table 9. When the homogenization speed was ≥1500 rpm and the homogenization dispersion time was ≥3 min, the blend uniformity of the suspension met the requirement of RSD ≤3.0%.

TABLE 9

Uniformity Test Result

| | | homogenization speed | | | | |
|---|---|---|---|---|---|---|
| | | 1000 rpm | 1000 rpm | 1500 rpm | 3000 rpm | 3000 rpm |
| | | | | Stirring speed | | |
| Process | | 20 rpm | 20 rpm | 20 rpm | 20 rpm | 20 rpm |
| | | | | Time | | |
| Parameters | | 3 min | 10 min | 3 min | 3 min | 20 min |
| Suspension State | | Uniform suspension, no visible aggregate particles, no residual powder on the liquid surface | Uniform suspension, no visible aggregate particles, no residual powder on the liquid surface | Uniform suspension, no visible aggregate particles, no residual powder on the liquid surface | Uniform suspension, no visible aggregate particles, no residual powder on the liquid surface | Uniform suspension, no visible aggregate particles, no residual powder on the liquid surface |

TABLE 9-continued

| | Uniformity Test Result | | | | |
|---|---|---|---|---|---|
| | homogenization speed | | | | |
| | 1000 rpm | 1000 rpm | 1500 rpm | 3000 rpm | 3000 rpm |
| | | | Stirring speed | | |
| | 20 rpm | 20 rpm | 20 rpm | 20 rpm | 20 rpm |
| Process | | | Time | | |
| Parameters | 3 min | 10 min | 3 min | 3 min | 20 min |
| Blend Uniformity in Suspension RSD* (n = 10) | 4.2% | 3.5% | 2.3% | 1.3% | 0.6% |
| Appearance of Dry Film | Uniform film without visible undispersed particles | Uniform film without visible undispersed particles | Uniform film without visible undispersed particles | Uniform film without visible undispersed particles | Uniform film without visible undispersed particles |

*Relative Standard Deviation

Example 8: Aripiprazole Soluble Film (Film with Different Particle Sizes)

In this example, aripiprazole soluble films having different particle size (Particle Size $D_{90}$: 0.5-56.4 μm) were prepared via the method of Example 5, with the formulation below, except with homogeneous blending plus plate- and frame blending.

| | |
|---|---|
| Aripiprazole | 30.0 mg (60% w/w) |
| Hydroxyethyl Cellulose | 10 mg (20% w/w) |
| Polyvinyl Alcohol | 9 mg (18% w/w) |
| Titanium Dioxide | 0.5 mg (1% w/w) |
| Sucralose | 0.5 mg (1% w/w) |
| Purified Water | 50 mg (Removed during manufacturing process) |

With the same formulation and process, the flexibility of the film varied greatly with different particle sizes of aripiprazole. The results are shown in Table 10. The results show that small particle size ($D_{90} \leq 10.2$ μm) of aripiprazole leads to a uniform and flexible film.

Example 9: Aripiprazole Soluble Film (Adding Defoamer)

In this example, aripiprazole (particle Size $D_{90}$: 4.7 μm) soluble film was prepared via the method according to Example 5-3, except with homogeneous blending plus plate- and frame blending.

| | |
|---|---|
| Aripiprazole | 10.0 mg (25% w/w) |
| Hydroxyethyl Cellulose | 20.0 mg (50.0% w/w) |
| Copovidone | 9.0 mg (22.0% w/w) |
| Defoamer (Dimethicone, Colloidal Silica, Simethicone, Lauric Acid, Oleyl alcohol, Palmitic Acid) | 0.20 mg (0.5%) |
| Titanium Dioxide | 0.8 mg (2% w/w) |
| Purified Water | 60 mg (Removed during manufacturing process) |

With the same formulation and process, the defoaming efficiency of film forming solution and flexibility of the film varied greatly with different defoamers. The results are shown in Table 11. Dimethicone, simethicone, and oleyl

TABLE 10

| Preparation of Solution Film with Different Particle Sizes of Aripiprazole | | | | | | |
|---|---|---|---|---|---|---|
| | Particle Sizes ($D_{90}$) | | | | | |
| | 56.4 μm | 38.9 μm | 23.5 μm | 10.2 μm | 4.7 μm | 0.5 μm |
| Suspension State | Poor uniformity, have a lot of precipitate at the bottom | Poor uniformity, have few precipitate at the bottom | Uniform | Uniform | Uniform | Uniform |
| Blend Uniformity in Suspension RSD* (n = 10) | N/A | 5.8% | 3.8% | 1.3% | 0.7% | 0.6% |
| Film Formed | N/A | Brittle | Brittle | Flexible | Flexible | Flexible |
| Tensile Strength(N/mm$^2$) | N/A | N/A | 2 | 6 | 10 | 12 |

*Relative Standard Deviation alcohol all provided a good defoaming effect. In contrast, colloidal silica exhibited a poor defoaming effect, and lauric acid and palmitic acid made the film soft and sticky.

TABLE 11

Defoaming Time with Different Defoamers

| Defoamer | none | Dimethicone | Colloidal Silica | Simethicone | Lauric Acid | Oleyl alcohol | Palmitic Acid |
|---|---|---|---|---|---|---|---|
| Defoaming Time | 16 h | 4 h | 13 h | 5 h | 7 h | 6 h | 7 h |
| Film Formed | Flexible | Flexible | Flexible | Flexible | Soft and Sticky | Flexible | Soft and Sticky |

Example 10: Bioavailability of Aripiprazole Soluble Films

In this example, aripiprazole (particle Size $D_{90}$: 0.5 µm, 10.2 µm and 23.5 µm) soluble film was prepared according to Example 5, with the formulation shown in Table 12, except with homogeneous blending plus plate- and frame blending.

TABLE 12

Aripiprazole Formulation

| | Example | | |
|---|---|---|---|
| | 10-1 | 10-2 | 10-3 |
| | Particle Sizes $D_{90}$ | | |
| | 23.5 µm | 10.2 µm | 0.5 µm |
| Aripiprazole | 10.0 mg (40% w/w) | 10.0 mg (40% w/w) | 10.0 mg (40% w/w) |
| Hypromellose | 20.0 mg (50.0% w/w) | 20.0 mg (50.0% w/w) | 20.0 mg (50.0% w/w) |
| Hydroxyethyl Cellulose | 3.92 mg (9.8% w/w) | 3.92 mg (9.8% w/w) | 3.92 mg (9.8% w/w) |
| Newton | 0.04 mg (0.1%) | 0.04 mg (0.1%) | 0.04 mg (0.1%) |
| Dimethicone | 0.04 mg (0.1%) | 0.04 mg (0.1%) | 0.04 mg (0.1%) |
| Purified Water | 60 mg (Removed during manufacturing process) | 60 mg (Removed during manufacturing process) | 60 mg(Removed during manufacturing process) |

A human pharmacokinetic study was conducted on several volunteers. They were divided into 4 groups: (i) aripiprazole soluble films manufactured according to Examples 10-1, 10-2 or 10-3, 10 mg dosage; and (ii) aripiprazole oral tablets, 10 mg dosage. Aripiprazole oral tablets (ABILIFY®) were used as a gold standard for comparison. The blood samples were taken before administration (0 min), and 0.5 h, 1 h, 1.5 h, 2 h, 2.5 h, 3 h, 3.5 h, 4 h, 6 h, 8 h, 10 h, 12 h, 24 h, 48 h, 72 h, 96 h, 144 h, 192 h, 240 h after administration, respectively. The blood samples were then used to determine the aripiprazole plasma concentration via a sensitive and precise LC-MS/MS method and to calculate relative bioavailability of the soluble films. As shown in 3, each bioavailability of the soluble films prepared in Examples 10-1, 10-2, and 10-3 was 64%, 94%, and 108% of the oral tablets, respectively. Each $T_{max}$ for these three examples was 3.5 h, 3.0 h and 2.3 h, respectively, and the $T_{max}$ of tablets was 2.8 h.

The results show that by controlling the particle size, the bioavailability of aripiprazole in the body can be effectively improved, and at the same time, the peak time ($T_{max}$) can be shortened. When the particle size $D_{90} \leq 10.2$ µm, the bioavailability of aripiprazole oral soluble film was bioequivalent to aripiprazole tablets.

TABLE 13

Bioavailability Test with Different Films

| | Pharmacokinetic parameter | | | |
|---|---|---|---|---|
| | Tablets | Example 10-1 Group | Example 10-2 Group | Example 10-3 Group |
| | Reference | Test Group | Test Group | Test Group |
| Mean $T_{max}$ (h) | 2.8 | 3.5 | 3.0 | 2.3 |
| Mean $C_{max}$ (ng/ml) | 51.3 | 33.1 | 46.2 | 56.4 |
| Mean $AUC_{0\text{-}240\ h}$ (hr*ng/ml) | 1118.8 | 713.2 | 1054.5 | 1213.7 |
| Relatively bioavailability | — | 64% | 94% | 108% |

The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. An aripiprazole oral soluble film comprising: about 25% w/w of aripiprazole in a crystalline state, about 50% w/w of hydroxyethyl cellulose, about 22% w/w of copovidone, and about 0.5% of a defoamer, wherein 90% of the aripiprazole particles have a size <4.7 μm and are uniformly blended in the film without visible undispersed particles.

2. An aripiprazole oral soluble film comprising: about 40% w/w of aripiprazole in a crystalline state, about 50% w/w of hypromellose, about 9.8% w/w of hydroxyethyl cellulose, about 0.1% of dimethicone, wherein 90% of the aripiprazole particles have a size <10.2 μm or <0.5 μm, and are uniformly blended in the film without visible undispersed particles.

3. The aripiprazole oral soluble film according to claim 2, wherein 90% of the aripiprazole particles have a size <10.2 μm.

4. The aripiprazole oral soluble film according to claim 2, wherein 90% of the aripiprazole particles have a size <0.5 μm.

5. An aripiprazole oral soluble film comprising: about 60% w/w of aripiprazole in a crystalline state, about 20% w/w of hydroxyethyl cellulose, and about 18% polyvinyl alcohol, wherein 90% of the aripiprazole particles have a size <10.2 μm, or <4.7 μm, or <0.5 μm, and are uniformly blended in the film without visible undispersed particles.

6. An aripiprazole oral soluble film according to claim 5, wherein 90% of the aripiprazole particles have a size <10.2 μm.

7. The aripiprazole oral soluble film according to claim 5, wherein 90% of the aripiprazole particles have a size <4.7 μm.

8. The aripiprazole oral soluble film according to claim 5, wherein 90% of the aripiprazole particles have a size <0.5 μm.

* * * * *